(12) United States Patent
Kubalak et al.

(10) Patent No.: US 7,789,873 B2
(45) Date of Patent: Sep. 7, 2010

(54) URINARY CATHETER ASSEMBLY

(75) Inventors: Thomas P. Kubalak, Orono, MN (US);
Teena L. Broumand, Ojai, CA (US);
Paul L. Schulz, Plymouth, MN (US);
Robert Lutzke, Coon Rapids, MN (US);
Dennis Femrite, Andover, MN (US);
Timothy Palmer, Marine on St. Croix, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/909,747

(22) Filed: Aug. 2, 2004

(65) Prior Publication Data

US 2006/0025753 A1    Feb. 2, 2006

(51) Int. Cl.
*A61M 27/00* (2006.01)
*A61M 1/00* (2006.01)
*A61M 5/32* (2006.01)
*B65D 71/00* (2006.01)

(52) U.S. Cl. .................. 604/544; 604/540; 604/177; 206/571

(58) Field of Classification Search ......... 604/540–544, 604/171–172, 158, 163, 533, 523, 164.01, 604/326, 329; 206/571
See application file for complete search history.

(56) References Cited

U.S. PATENT DOCUMENTS

| | | | | |
|---|---|---|---|---|
| 3,335,723 A * | 8/1967 | Waldman, Jr. | ............... | 604/163 |
| 3,770,128 A * | 11/1973 | Kast | ............... | 210/167.26 |
| 3,854,483 A * | 12/1974 | Powers | ............... | 604/172 |
| 3,894,540 A * | 7/1975 | Bonner, Jr. | ............... | 604/171 |
| 4,062,363 A * | 12/1977 | Bonner, Jr. | ............... | 604/171 |
| 4,170,996 A * | 10/1979 | Wu | ............... | 604/171 |
| 4,230,115 A * | 10/1980 | Walz et al. | ............... | 604/517 |
| 4,698,057 A * | 10/1987 | Joishy | ............... | 604/176 |
| 4,767,409 A * | 8/1988 | Brooks | ............... | 604/171 |
| 4,811,847 A * | 3/1989 | Reif et al. | ............... | 206/571 |
| 4,858,821 A * | 8/1989 | Bickelhaupt | ............... | 229/123.1 |
| 5,392,918 A * | 2/1995 | Harrison | ............... | 206/571 |
| 5,715,815 A * | 2/1998 | Lorenzen et al. | ............... | 128/207.14 |
| 5,836,918 A * | 11/1998 | Dondlinger | ............... | 604/171 |
| 6,132,408 A * | 10/2000 | Lutz | ............... | 604/335 |
| 6,217,569 B1 | 4/2001 | Fiore | | |
| 6,905,484 B2 * | 6/2005 | Buckman et al. | ............... | 604/174 |
| 7,083,598 B2 * | 8/2006 | Liska | ............... | 604/180 |
| 7,524,511 B1 * | 4/2009 | Kleyne | ............... | 424/401 |
| 2002/0103460 A1 * | 8/2002 | Kubalak et al. | ............... | 604/171 |
| 2003/0004496 A1 | 1/2003 | Tanghoej | | |

(Continued)

FOREIGN PATENT DOCUMENTS

EP    1023882    8/2000

(Continued)

*Primary Examiner*—Tatyana Zalukaeva
*Assistant Examiner*—Susan Su
(74) *Attorney, Agent, or Firm*—Coloplast Corp., Coloplast A/S; Daniel G. Chapik; Nicholas R. Baumann (57) ABSTRACT

A urinary catheter assembly that can reduce the need for a user to handle the urinary catheter directly, thereby reducing the likelihood of a urinary tract infection and making the catching process less messy. In one aspect, a urinary catheter apparatus and methods for voiding a human's bladder and enabling a human patient to void his or her bladder are provided.

24 Claims, 6 Drawing Sheets

U.S. PATENT DOCUMENTS

| | | | |
|---|---|---|---|
| 2003/0018322 A1 * | 1/2003 | Tanghoj et al. | 604/544 |
| 2004/0243104 A1 * | 12/2004 | Seddon | 604/540 |
| 2005/0242252 A1 * | 11/2005 | DiMaggio | 248/206.1 |
| 2006/0058777 A1 * | 3/2006 | Nielsen | 604/544 |

FOREIGN PATENT DOCUMENTS

| | | | |
|---|---|---|---|
| WO | WO 94/16747 A1 * | 8/1994 | |
| WO | WO 96/30277 A1 * | 10/1996 | |
| WO | WO 98/06642 | 2/1998 | |
| WO | WO 98/11932 | 3/1998 | |
| WO | WO 00/30575 | 6/2000 | |
| WO | 2004/054653 | 7/2004 | |

* cited by examiner

URINARY CATHETER ASSEMBLY

TECHNICAL FIELD

This document relates to urinary catheters.

BACKGROUND

Many people take for granted how easy it is to void their bladders. For others, the process of voiding their bladders can be cumbersome. Many people, including those who have had traumatic spinal cord injuries, must use a urinary catheter to void their bladders. Such people must insert, or have a caregiver insert, the urinary catheter into their urethras and into their bladders. From there, the person can void his or her bladder, draining the urine into an appropriate drainage receptacle.

Urinary catheters are disposable. As such, users often carry multiple urinary catheters with them when they are away from home for an extended period of time. In addition, users are often required to carry various accessories such as extension tubes to aid in the cathing process. The urinary catheters and/or the accessories can consume a considerable amount of space.

Urinary tract infections can be common among people who void their bladders by using a urinary catheter. The urinary catheter can become contaminated as it is exposed to a non-sterile environment (e.g., the user's hands and/or urethral meatus). The risk of contamination can be especially high among wheelchair patients. Such patients' hands regularly contact their wheelchair wheels, which can contact unsanitary surfaces of all kinds. Furthermore, it can be difficult to handle a lubricated urinary catheter directly with one's hands since the lubrication can cause the urinary catheter to slip from a user's grasp.

People drain urine through urinary catheters into several different kinds of drainage receptacles. It is not uncommon for the urinary catheter or other drainage tube to withdraw from the drainage receptacle during the drainage process. This withdrawing can result in urine being spilled.

In some cases, users lubricate the urinary catheters before inserting them into the urethra. Applying lubrication to the urinary catheters can be messy. Some urinary catheters can be pre-lubricated. In some cases, pre-lubricated catheters can become too dry by the time the user is ready to begin the cathing process. This can result in considerable patient discomfort while the urinary catheter is being inserted into the patient's urethra.

SUMMARY

This document describes a urinary catheter assembly that can reduce the need for a user to handle the urinary catheter directly, thereby reducing the likelihood of a urinary tract infection and making the cathing process less messy. In one aspect, a urinary catheter apparatus and methods for voiding a human's bladder and enabling a human patient to void his or her bladder are provided. The apparatus includes a urinary catheter. The urinary catheter can have a proximal end portion defining a urine inlet opening. The urinary catheter can have a distal end portion defining a urine outlet opening. The apparatus includes a sheath. The sheath can have a front end portion defining a front opening. The sheath can have a rear end portion defining a rear opening. The apparatus can be configured such that at least a portion of the urinary catheter is within the sheath during storage. The apparatus can be configured such that the distal end portion moves toward the front end portion during use, thereby increasing the distance between the distal end portion and the rear end portion. During use, urine can flow into the urine inlet opening, out of the urine outlet opening, and out of the rear opening.

The urinary catheter can be between fifteen and fifty-five centimeters in length. The urinary catheter can be made of polyvinyl chloride. The proximal end portion can define a second urine inlet opening. The urine outlet opening can be oval-shaped. The distal end portion can define the urine outlet opening at the end of the urinary catheter.

The sheath can be made of polyvinyl chloride The front end portion can define the front opening at the end of the sheath. The apparatus can be configured such that the urinary catheter is completely within the sheath during storage. The front opening and the back opening can be sealed during storage. The apparatus can be configured such that, during storage, the proximal end portion is proximate to the front end portion and the distal end portion is proximate to the rear end portion. The apparatus can be configured such that the distal end portion stops moving at a position that is nearer to the front end portion than the rear end portion. The apparatus can be configured such that at least a portion of the urinary catheter remains within the sheath during use. During use, urine can flow out of the urine outlet opening, along the lumen of the sheath toward the rear opening, and out of the rear opening.

The apparatus can include a package enclosing the urinary catheter and the sheath during storage. The package can be sized to fit within a cavity having a length of seventeen centimeters, a width of twelve centimeters, and a thickness of three centimeters. The urinary catheter and the sheath can be coiled inside the package. The apparatus can include a hermetically-sealed container to contain the package during storage. The apparatus can include a distal end connector that defines a distal connector opening. The distal end connector can be attached to the distal end portion. The apparatus can include a front end connector that defines a front connector opening. The front end connector can be attached to the front end portion.

During use, the apparatus can be configured such that the distal end connector interfaces with the front end connector, thereby forming a seal to allow urine to flow out of the urine outlet opening, through the distal connector opening and the front connector opening, and out of the rear opening. The apparatus can include a rear end connector that defines a rear connector opening. The rear end connector can be attached to the rear end portion. During use, urine can flow out of the rear opening and out of the rear connector opening. The rear end connector is operable to connect to an extension tube or a collection bag.

The apparatus can include a fastening mechanism attached to the rear end connector. During use, the fastening mechanism can fasten the rear end connector to a drainage receptacle whether the surface of the drainage receptacle is wet or dry. The fastening mechanism can include a suction cup. The apparatus can include a handle attached to the rear end connector. During use, the apparatus can be configured such that the handle is actuated to disengage the rear end connector from the drainage receptacle.

The apparatus can include an introducer tip that defines an insertion opening. The introducer tip can be attached to the front end portion. During use, the apparatus can be configured such that the proximal end portion protrudes through the front opening and the insertion opening. The apparatus can include a lubricant. The apparatus can be configured such that at least a portion of the urinary catheter is coated with a lubricant. The lubricant can include a water-based lubricant.

The method for voiding a human's bladder can include positioning a catheter assembly proximate to the urethral meatus of a human patient. The catheter assembly can be the urinary catheter apparatus. The method for voiding a human's bladder can include moving the distal end portion toward the front end portion, thereby advancing the proximal end portion into the urethra of the human patient and increasing the distance between the distal end portion and the rear end portion. The method for voiding a human's bladder can include draining urine through the urine inlet opening, the urine outlet opening, and the rear opening.

The method for voiding a human's bladder can include connecting an extension tube or a collection bag to the rear end connector. The method for voiding a human's bladder can include fastening the rear end connector to a drainage receptacle, whether the surface of the drainage receptacle is wet or dry, using the fastening mechanism. The method for voiding a human's bladder can include actuating the handle to disengage the rear end connector from the drainage receptacle. The method for voiding a human's bladder can include advancing the proximal end portion through the front opening and the insertion opening. The method for voiding a human's bladder can include removing the urinary catheter from the urethra of the human patient. Removing the urinary catheter from the urethra of the human patient can involve moving the distal end portion toward the back end portion, thereby increasing the distance between the distal end portion and the front end portion. The method for voiding a human's bladder can include removing the catheter assembly from a package. The method for voiding a human's bladder can include uncoiling the catheter assembly. The method for voiding a human's bladder can include removing the package from a hermetically-sealed container.

The method for enabling a human patient to void his or her bladder can include applying lubrication to at least a portion of the urinary catheter. The method for enabling a human patient to void his or her bladder can include placing at least a portion of the urinary catheter in the sheath. The method for enabling a human patient to void his or her bladder can include placing the sheath and the urinary catheter in a package.

In the method for enabling a human patient to void his or her bladder, lubricating the urinary catheter can occur before placing the urinary catheter in the sheath. The method for enabling a human patient to void his or her bladder can include coiling the sheath and the urinary catheter before placing the sheath and the urinary catheter in the package. The method for enabling a human patient to void his or her bladder can include stripping the urinary catheter before applying lubricant to the at least a portion of the urinary catheter. Such stripping can include steam cleaning the urinary catheter. The method for enabling a human patient to void his or her bladder can include placing the package in a hermetically-sealed container. The method for enabling a human patient to void his or her bladder can include providing the container to a patient. The method for enabling a human patient to void his or her bladder can include providing the package to a patient.

Certain embodiments can provide one or more of the following advantages. In some embodiments, the catheter assembly can be designed such that the need for a user to touch the urinary catheter directly with his or her hands can be reduced or eliminated. In such embodiments, the likelihood of a urinary tract infection can be reduced. In such embodiments, the user can avoid the mess of touching a lubricated urinary catheter. In such embodiments, the user can maneuver the catheter assembly more easily. In some embodiments, the catheter assembly can be placed in a pocket-sized package for transport. In some embodiments, the catheter assembly can be designed to prevent withdrawal from the drainage receptacle during drainage. Such embodiments can reduce the likelihood of spilling urine during drainage. In some embodiments, the catheter assembly can be designed such that the urinary catheter does not contact the patient's urethral meatus during insertion. In some embodiments, the urinary catheter can be pre-treated to increase the likelihood that lubrication will adhere to the urinary catheter. In some embodiments, lubricant can be used that does not evaporate quickly.

The details of one or more embodiments are set forth in the accompanying figures and the description below. Other features, objects, and advantages will be apparent from the description and figures, and from the claims.

DESCRIPTION OF FIGURES

Like reference symbols in the various figures indicate like elements.

DETAILED DESCRIPTION

Figure 1:
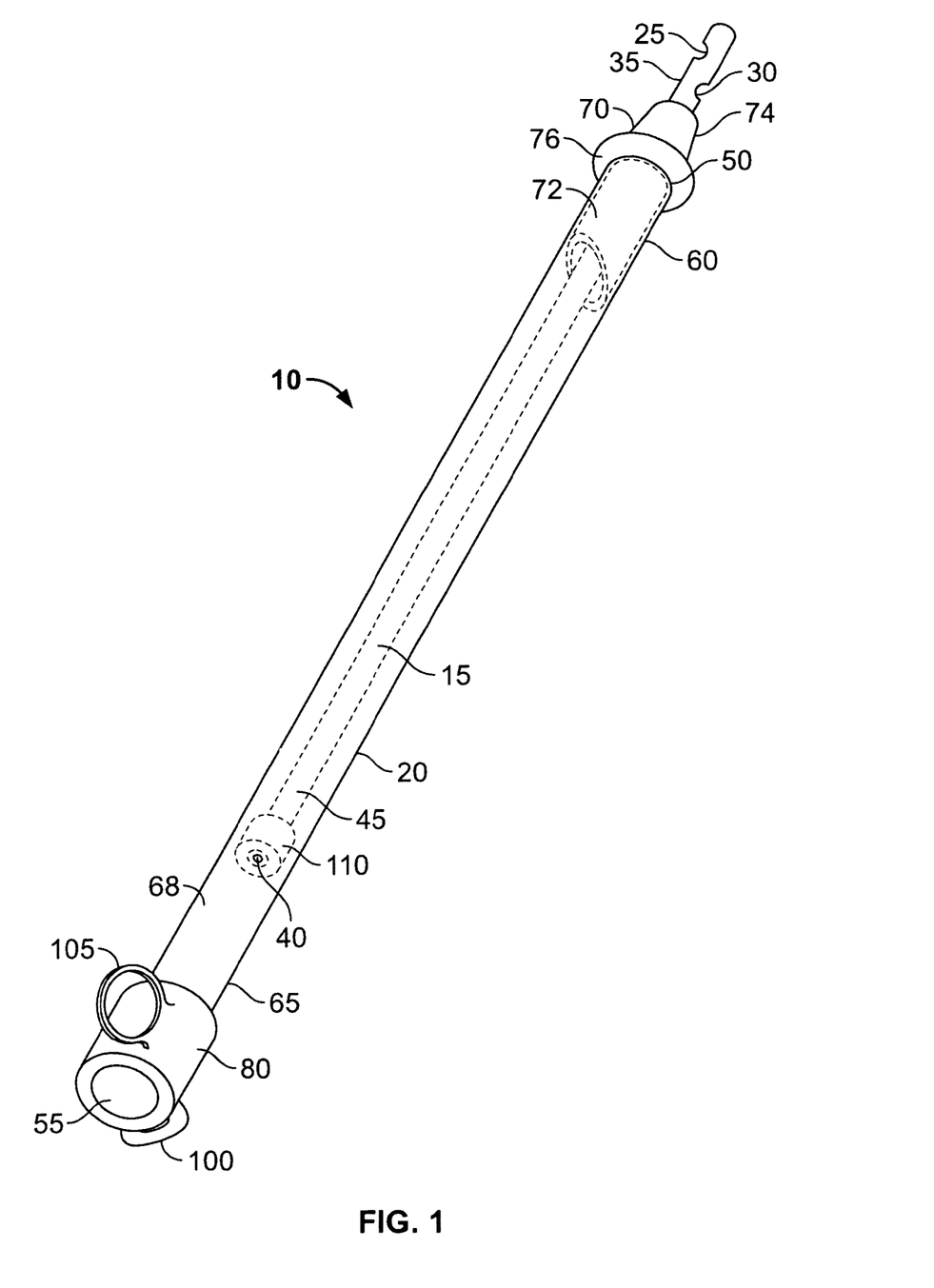
FIG. 1 is a perspective view of a catheter assembly.

FIG. 1 is a perspective view of a catheter assembly 10. The catheter assembly 10 can include a urinary catheter 15 and a sheath 20. The urinary catheter 15 can be made of polyvinyl chloride (PVC), polyurethane, silicon rubber, nitrile rubber, or other appropriate material. The urinary catheter 15 can have a polished surface. The urinary catheter can be between fifteen and fifty-five centimeters in length and between fifteen and seventy millimeters in diameter.

In one embodiment, the urinary catheter 15 can have two openings 25, 30 at the proximal end portion 35 and one opening 40 at the distal end portion 45. Any number of openings can be implemented. For example, the proximal end portion 35 can have one, two, three, four, five, or more openings.

Figure 2:
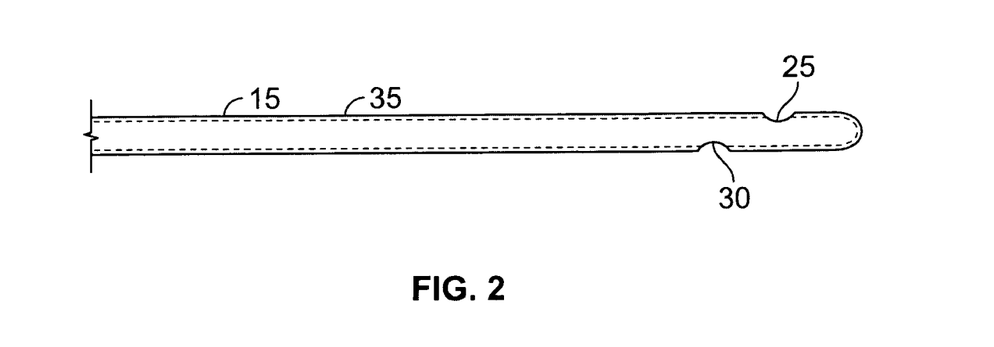
FIG. 2 is a close-up side view of the proximal end portion of a urinary catheter.

FIG. 2 is a close-up view of the proximal end portion 35 of the urinary catheter 15. The openings 25, 30 can be positioned such that one of the openings 25 is closer to the end of the urinary catheter 15 than is the other opening 30. One of the openings 25 can be spaced 180 degrees about the outer surface of the urinary catheter 15 from the other opening 30. If there are multiple openings, the multiple openings can be positioned in a variety of ways. For example, the openings can be positioned along the same longitudinal line. The openings can be positioned equidistant from the end of the urinary catheter 15. The openings can be positioned according to any combination of spacing about the outer surface of the urinary catheter 15 and distance from the end of the urinary catheter 15. In some embodiments, the end of the urinary catheter 15 can be open, constituting an opening. In such embodiments, the opening in the end of the urinary catheter 15 can have a diameter equal to the inner diameter of the urinary catheter 15. Alternatively, such opening in the end can have a smaller diameter (e.g., a diameter that is half the diameter of the inner cross-section of the urinary catheter 15).

As shown in FIGS. 1-2, the two openings 25, 30 at the proximal end portion 35 are oval-shaped. The openings 25, 30 can be any appropriate shape, such as circular or rectangular. Also, if multiple openings are present, each opening can be configured in a different shape.

Figure 3:
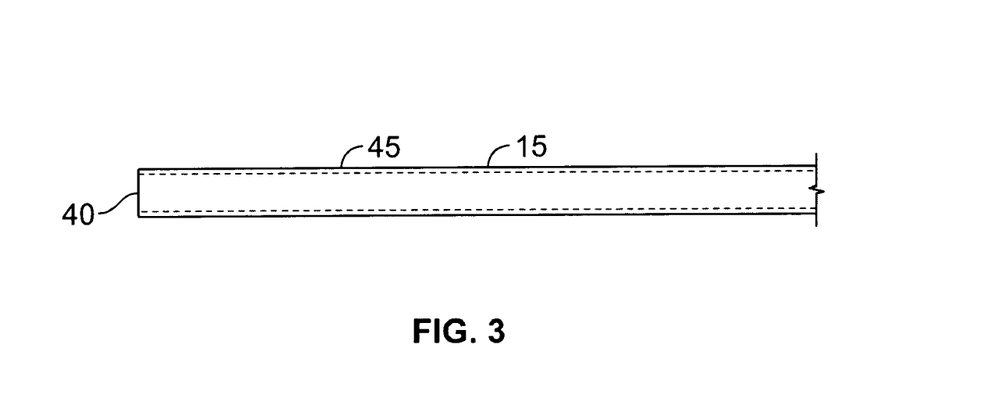
FIG. 3 is a close-up side view of the distal end portion of a urinary catheter.

Referring to FIG. 1, the end of the distal end portion 45 of the urinary catheter 15 can be open, constituting the opening 40. FIG. 3 is a close-up view of the distal end portion 45 of the urinary catheter 15. As shown, the diameter of the opening 40 can be equal to the inner diameter of the urinary catheter 15. As with the openings 25, 30 in the proximal end portion 35, the opening 40 in the distal end portion 45 can be configured in many forms. For example, multiple openings can be defined in the distal end portion 45. In such an embodiment, one of the openings can be attached to a device that collects urine samples, and the other opening can be used to drain the excess urine into a drainage receptacle. Each such opening can be positioned in various places in the distal end portion 45. Also as with the openings 25, 30 in the proximal end portion 35, the opening 40 in the distal end portion 45 can be configured in several shapes.

Referring to FIG. 1, the sheath 20 can be made of PVC, polyvinyl alcohol (PVA), silicon rubber, polyurethane, or other appropriate material. The sheath 20 can be a semi-flexible tube or cylinder with various cross-sectional shapes, can be a flexible sleeve that is able to be flattened when laid on its side, or can take any other appropriate shape. The sheath may be constructed of two flat sheets bonded together to create a passage between the two sheets. In some embodiments, the sheath 20 can be extruded to form a continuous cross-section. The sheath 20 can be collapsible longitudinally. In the embodiment of FIG. 1, the sheath 20 has two openings 50, 55. One of the openings 50 is at the end of the front end portion 60. The other opening 55 is at the end of the rear end portion 65. More openings are possible. The openings 50, 55 can be configured in different positions. For example, in some embodiments, a sheath 20 can have two or more openings in the front end portion 60 and two or more openings in the rear end portion 65. In such embodiments, the same sheath model can be used for urinary catheters of various lengths. In some embodiments, the openings 50, 55 can be sealed during storage. In such embodiments, a user can un-seal the appropriate openings 50, 55 for use.

The urinary catheter 15 can be designed to fit within the sheath 20. The urinary catheter can be slid back and forth within the lumen 68 of the sheath 20. The urinary catheter 15 can be sized to slide into and out of the opening 50 in the front end portion 60. The opening 55 in the rear end portion 65 can be designed such that the urinary catheter 15 is not able to slide into and out of the opening 55 in the rear end portion 65. In some embodiments, the urinary catheter 15 can slide into or out of both openings 50, 55 in the sheath 20. In some embodiments, during storage, a considerable section (e.g., 1, 2, 3, 4, 5, 6, 7, 8, 9, 10, 15, 20, 25, or more percent) of the urinary catheter 15 can project from the opening 50 in the front end portion 60 of the sheath 20, from the opening 55 in the rear end portion 65 of the sheath, or from both openings 50, 55.

Figure 4:
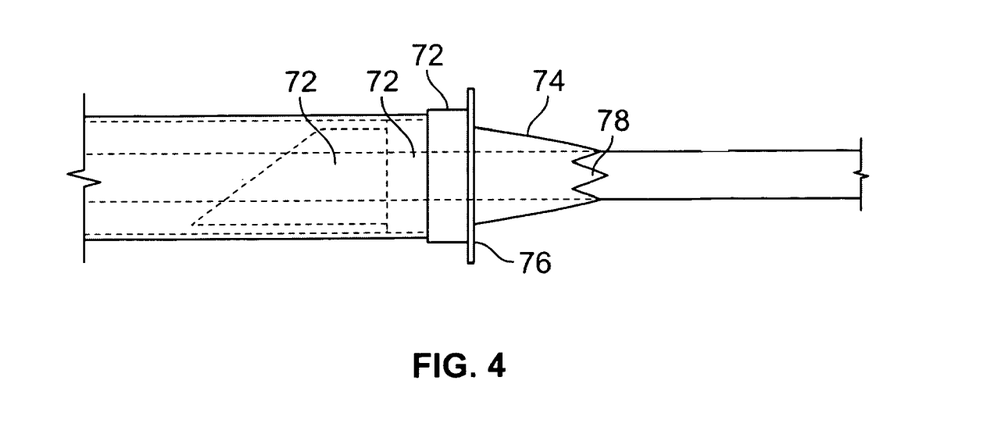
FIG. 4 is a close-up side view of a urinary catheter partially within an introducer tip.

The front end portion 60 of the sheath 20 can be attached to an introducer tip 70. The introducer tip 70 can make it easier for patients to insert the urinary catheter 15 into their urethras—a process that will be discussed in more detail in conjunction with FIGS. 9A-9C. The introducer tip 70 can allow patients to insert the urinary catheter 15 into their urethras without having to touch the urinary catheter 15 with their hands. Touching the urinary catheter 15 with their hands, and subsequently touching the urinary catheter 15 to their urethral meatuses can transmit germs to their urethral meatuses, which can lead to urinary tract infections. FIG. 4 is a close-up view of a urinary catheter 15 extending through introducer tip 70. The introducer tip 70 can be designed to receive the urinary catheter 15. The urinary catheter 15 can be designed to slide into and out of the introducer tip 70. At least a section of the receiving portion 72 of the introducer tip 70 can be attached to the inside surface of the sheath 20, to the outside surface of the sheath 20, or to both surfaces of the sheath 20. The receiving portion 72 of the introducer tip 70 can provide a more rigid channel for guiding the urinary catheter 15 toward, and out of, the opening 50 in the front end portion 60 of the sheath 20. In some embodiments, a cap can cover part or all of the insertion portion 74 of the introducer tip 70. In such embodiments, the cap can include a handle to allow for simpler removal. The handle can be a ring that can be pulled by a user with one finger.

The insertion portion 74 of the introducer tip 70 can be shaped to complement the shape of a human patient's urethral meatus. A rounded cone-shape is shown, but many shapes are possible. For example, a straight-sided tube or a cone with stabilization members for engaging the surrounding skin can be used. The introducer tip 70 can be designed to include triangular flaps 78. The triangular flaps 78 can stabilize the urinary catheter 15 as the urinary catheter 15 slides into and out of the introducer tip 70. The attached bases of the triangular flaps 78 can combine to form a square. The detached opposed corners can be disposed toward the inside of the square, meeting at the center. In such a configuration, as a urinary catheter 15 moves out of the introducer tip 70, the four triangular flaps are deflected but maintain pressure on the outer surface of the urinary catheter 15. This pressure can help stabilize the urinary catheter 15. Configurations other than triangular flaps also can be used. For instance, a plurality of rods may project radially from the inner surface of the introducer tip 70 toward the center of the introducer tip 70.

A flange 76 can separate the introducer tip's receiving portion 72 from its insertion portion 74. The flange 76 can serve as a stopping point for patients as they insert the introducer tip 70 into their urethral meatuses. Patients can hold onto the flange as they press the introducer tip 70 against their urethral meatuses. In some embodiments, an introducer tip 70 of continuous cross section can be implemented. In such embodiments, flanges are not provided. In such embodiments, the patient may be required to monitor how far to insert the introducer tip 70.

Other accessories that cap the front end portion 60 of the sheath 20 can be used. For example, in some embodiments, a flap can be implemented. In some embodiments, the interface between the flap and the sheath can be perforated. In such embodiments, the flap can be designed with a handle. The handle can be a ring that can be pulled by a user with one finger. In some embodiments, the end of the front end portion 60 of the sheath 20 can be sealed. In such embodiments, a user can cut the end of the sheath 20 with, for example, scissors. These and other suitable accessories can be configured in combination with introducer tips.

Figure 5A:
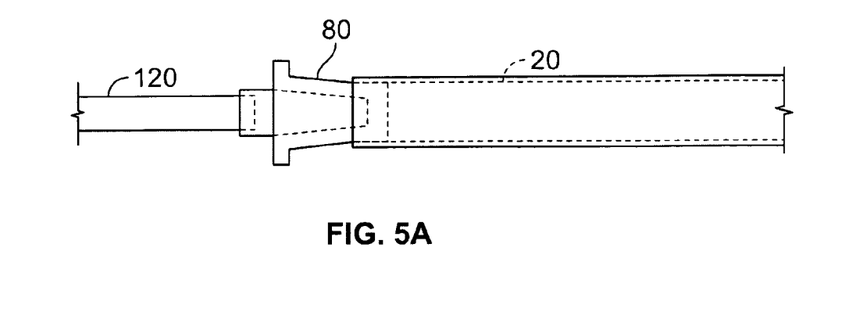
FIG. 5A is a side view of a sheath connector connected to an extension tube.

Referring to FIG. 1, the rear end portion 65 of the sheath 20 can be attached to a sheath connector 80. The sheath connector 80 can attach to either the inner or outer surface, or both surfaces, of the sheath 20. The sheath connector 80 can have an opening in both of its ends. The sheath connector's 80 openings can align with the lumen 68 of the sheath 20, allowing urine to flow through the lumen 68 and through the sheath connector 80. The sheath connector 80 can be designed to attach to various accessories. FIG. 5A shows a sheath connector 80 connected to an extension tube 120. The extension tube 120 can be attached at its other end to a drainage receptacle. In some embodiments, the extension tube 120 can allow patients to be situated further away from the drainage receptacle during drainage than if the sheath 20 were attached to the drainage receptacle.

Figure 5B:
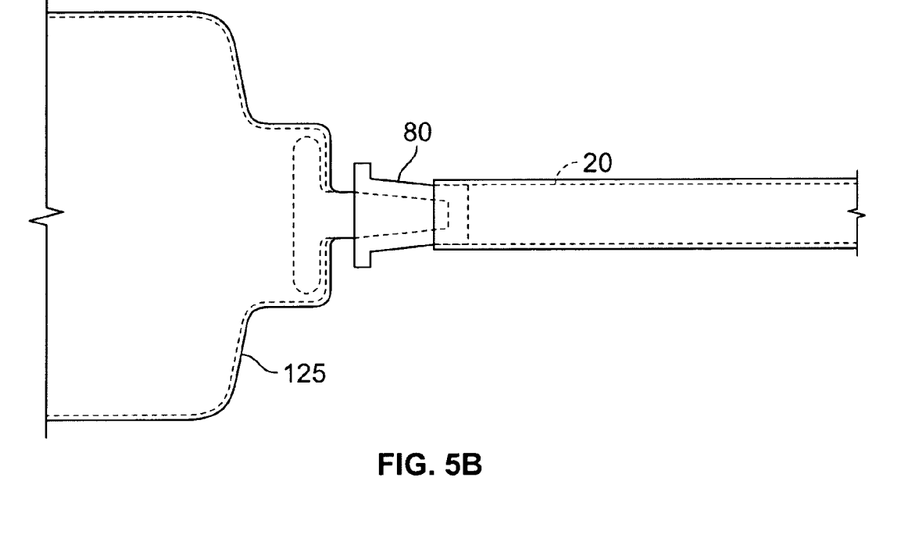
FIG. 5B is a side view of a sheath connector connected to a collection bag.

FIG. 5B shows a sheath connector 80 connected to a collection bag 125. The collection bag 125 can be equipped with one or more straps. The straps can be designed to secure the collection bag 125 to the patient's person (e.g., to the patient's leg). The collection bag 125 can assist a patient who is in a location in which draining into a toilet would be inconvenient. In such a situation, the patient can drain urine into the collection bag 125 and then carry the collection bag 125 on his or her person until draining into a toilet would be convenient. The collection bag 125 can be designed such that the volume of urine is maintained in a relatively flat position within the collection bag 125. This can allow the patient to carry the filled collection bag 125 in a discrete manner. Other accessories, such as a collection cup, a bed pan, and an extension tube, can be connected to the sheath connector 80.

Figure 5C:
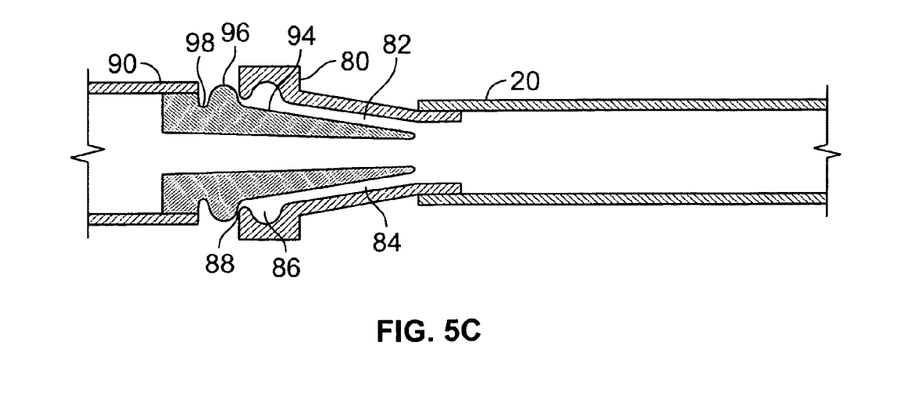
FIG. 5C is a cross-sectional view of a configuration in which a sheath connector can connect to an accessory.

FIG. 5C shows a close up cross-sectional view of an exemplary configuration in which a sheath connector 80 connects to an accessory 90. The sheath connector 80 can have an accessory receiving portion 82. The accessory receiving portion 82 can be designed to include a nose channel 84. The accessory receiving portion 82 can be designed to include a plate channel 86. The accessory receiving portion 84 can be designed to include a lip section 88. The accessory 90 can include an accessory connector 92. The accessory connector 92 can be configured to include a nose section 94. The accessory connector 92 can be configured to include a plate section 96. The accessory connector 92 can be configured to include a lip channel 98. Both the sheath connector 80 and the accessory connector 92 can be made of relatively elastic material.

To connect the sheath connector 80 to the accessory 90, a user can insert the nose section 94 partway into the nose channel 84 until the plate section 96 contacts the lip section 88. The plate section 96 can be pressed flush against the lip section 88. The user can apply force along the longitudinal axis into the accessory receiving portion 82 of the sheath connector 80. Such force can cause the plate section 96 to squeeze past the lip section 88. When the plate section 96 squeezes past the lip section 88, the nose channel 84 can engage the nose section 94, the plate channel 86 can engage the plate section 96, and the lip channel 98 can engage the lip section 88. This configuration can secure the sheath connector 80 to an accessory. Many other configurations can be implemented.

Referring to FIG. 1, the sheath connector 80 can be designed to house a suction cup 100. The suction cup 100 can be configured to secure the sheath connector 80, and thereby the rear end portion 65 of the sheath 20, to a drainage receptacle. Such drainage receptacles can include toilets, collection cups, or other suitable receptacles. Although a suction cup 100 is shown, the sheath connector 80 can be secured to a drainage receptacle in many ways. For example, if a collection cup is used, the sheath connector 80 can be secured to the collection cup by a snap, Velcro, a button/slot configuration, removable adhesive, a corresponding connector, or other appropriate fasteners. If a toilet is used as a drainage receptacle, the sheath connector 80 can be secured to the toilet by a bracket that mounts to the bowl, by a flange that prevents the sheath connector 80 from withdrawing when the sheath 20 is placed between the top of the bowl and the bottom of the seat, by a corresponding connector mounted to the toilet, or by any other appropriate fasteners.

The sheath connector 80 can include a handle 105. The handle 105 can be actuated to disengage the suction cup 100 from the drainage receptacle. Such actuation can involve a user inserting his or her finger within the handle 105, gripping the handle 105, and pulling the handle 105 away from the drainage receptacle. The handle 105 can be integrally formed of the same material as the sheath connector 80, such as by injection molding. The handle 105 can be used to engage the suction cup 100 to the drainage receptacle. As shown, the handle 105 can be spaced 180 degrees about the outer surface of the sheath connector 80 from where the suction cup 100 attaches to the sheath connector 80. Such an embodiment can allow a patient to pull on the handle 105 without touching the drainage receptacle, which can often be unsanitary.

A patient can disengage the suction cup 100 in ways other than actuating a handle 105. For instance, one or more tabs can be provided on which a user may pull to expose air to the underside of the suction cup. Such pulling can equalize the pressure above and below the suction cup 100, thereby disengaging the suction cup 100. In some embodiments, a patient can disengage the suction cup 100 by sliding the sheath connector 80, and thus the suction cup 100, until the suction cup 100 no longer contacts a uniform surface. In such embodiments, the contact with the non-uniform surface would produce equalized above- and below-suction-cup pressure to disengage the suction cup 100. In some embodiments, a patient can grip the sides of the sheath connector 80 and pull up to disengage the suction cup 100. Other suitable alternatives can be used. For non-suction cup fastening mechanisms, appropriate disengagement mechanisms can be provided.

Figure 6:
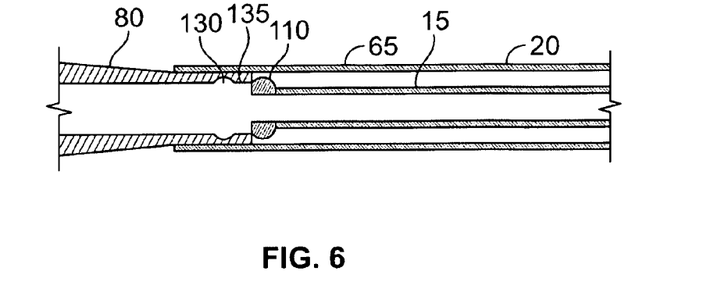
FIG. 6 is a cross-sectional view of a configuration in which a catheter connector 110 can couple to a sheath connector.

The distal end portion 45 of the urinary catheter 15 can be designed to attach to a catheter connector 110. The catheter connector 110 can attach to the inner or outer surface, or both surfaces, of the urinary catheter 15. The catheter connector 110 can have an opening in both of its ends. The openings can align with the lumen 115 of the urinary catheter 15 through which urine may flow. In some embodiments, during storage, the catheter connector 110 can couple to the sheath connector 80. FIG. 6 is an exemplary close-up, cross-sectional view of such an embodiment. As shown, a sheath connector 80 is configured differently than the sheath connector of FIG. 5C. In FIG. 6, the urinary catheter 15 is positioned such that the distal end portion 45 is proximate to the rear end portion 65 of the sheath 20. The sheath connector 80 can be designed to include a catheter connector channel 130. The sheath connector 80 can be designed to include a ridge section 135. The catheter connector 110 can be designed such that the catheter connector channel 130 can receive the catheter connector 110. The catheter connector 110 and the sheath connector 80 can be made of relatively elastic material.

To couple the catheter connector 110 to the sheath connector 80, a user can apply force to the urinary catheter 15 along the longitudinal axis toward the sheath connector 80. The force can cause the catheter connector 80 to squeeze past the ridge section 135. When the catheter connector 80 squeezes past the ridge section 135, the catheter connector channel 130 can receive the catheter connector 110. In such embodiments, the coupling can hold the urinary catheter 15 in place. The coupling shown in FIG. 6 is exemplary; the catheter assembly can be designed to include any kind of appropriate coupling.

Figure 7:
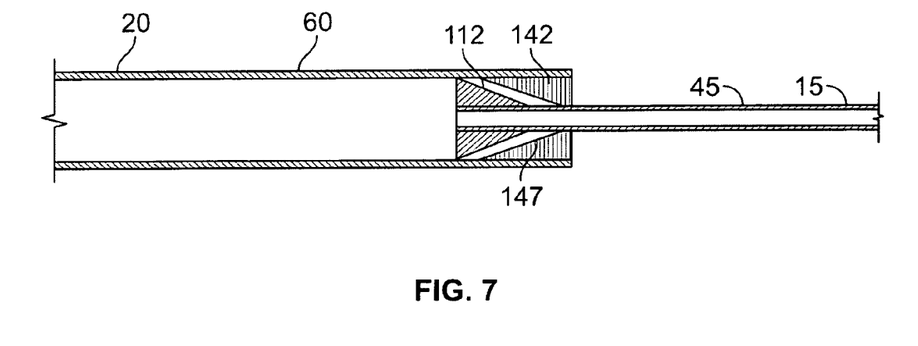
FIG. 7 is a cross-sectional view of a configuration in which a catheter connector can engage a front sheath connector.

Referring again to FIG. 1, the catheter connector 110 can slide within the sheath 20. In some embodiments, in use, the catheter connector 110 can engage the introducer tip 70 or some other form of connector. The introducer tip 70 can be a connector. FIG. 7 is an exemplary close-up, cross-sectional view of how a catheter connector 112 can engage a connector other than an introducer tip. The urinary catheter 15 can be positioned such that the distal end portion 45 is proximate to the front end portion 60 of the sheath 20. A front sheath connector 142 can be attached to the inside surface, the outside surface, or both surfaces of the sheath 20. The front sheath connector 142 can be designed to include a funneled receptacle 147. The funneled receptacle 147 can be designed to engage the catheter connector 112. The catheter connector 110 and the front sheath connector 140 can be made of relatively elastic material.

To connect the catheter connector 110 to the front sheath connector 142, a user can apply force to the sheath 20 along the longitudinal axis away from the urinary catheter 15. The force can cause the catheter connector 112 to press into the funneled receptacle 147. As the catheter connector 112 presses into the funneled receptacle 147, frictional forces maintain the catheter connector 112 in position. In such embodiments, the interface between the catheter connector 112 and the introducer tip or other connector can form a liquid-tight seal, preventing urine from leaking between the inner surface of the front sheath connector 142 and the outer surface of the urinary catheter 15. Such leaking can pose a problem when the front end portion 60 of the sheath 20 is not maintained at a higher elevation than other portions of the sheath 20. Patients who void their bladders while lying down can have difficulty maintaining the front end portion 60 for the sheath 20 at such a high elevation. The configuration shown in FIG. 7 is exemplary; the catheter assembly can be designed to include any kind of appropriate connection between the catheter connector 112 and an introducer tip or other form of connector.

Referring again to FIG. 1, a suction cup 100 or other fastening mechanism can be mounted on the catheter connector 110. In such embodiments, the catheter connector 110 can be fastened to, and detached from, a drainage receptacle in any of the manners described above or in any other appropriate manner.

The urinary catheter 15 can be placed within the sheath 20 in several different configurations during storage. The proximal end portion 35 of the urinary catheter 15 can be near the front end portion 60 of the sheath 20. The distal end portion 35 of the urinary catheter 15 can be near the rear end portion 15 of the sheath 20. In some embodiments, the urinary catheter 15 can fit completely within the sheath 20. In such embodiments, the openings 50, 55 in the sheath 20 can be sealed during storage. In such embodiments, users can break the seals and expose the openings 50, 55 for use. In some embodiments, a section of the urinary catheter 15 can project from the opening 50 in the front end portion 60 of the sheath 20. In such embodiments, the section of the urinary catheter 15 that projects from the opening 50 in the front end portion 60 of the sheath 20 can be designed to be contained within the introducer tip 70. In some embodiments, a section of the urinary catheter 15 can project from the opening 55 in the rear end portion 65 of the sheath 20. In such embodiments, the section of the urinary catheter 15 that projects from the opening 55 in the rear end portion 65 of the sheath 20 can be designed to be contained within the sheath connector 80. In some embodiments, sections of the urinary catheter 15 can project from both openings 50, 55 of the sheath 20. In such embodiments, the sections of the urinary catheter 15 that project the openings 50, 55 of the sheath 20 can be contained within the introducer tip 70 and the sheath connector 80, respectively.

Figure 8A:
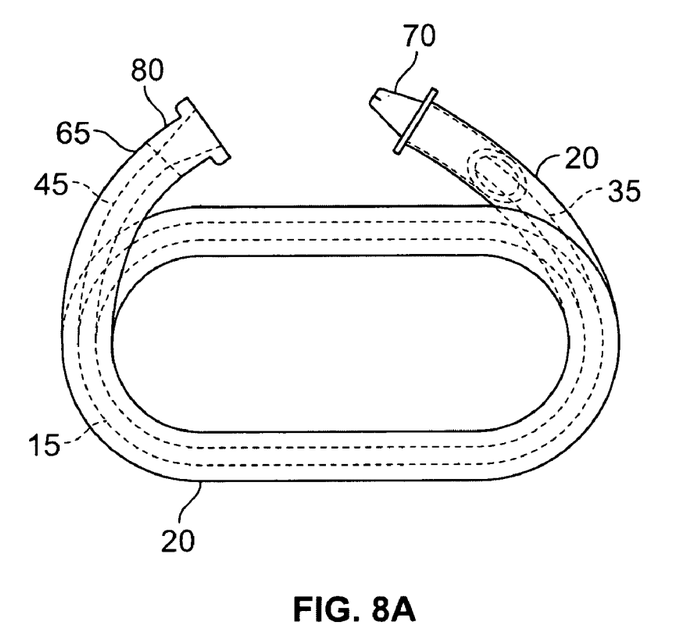
FIG. 8A is a top view of a catheter assembly in a coiled configuration

The catheter assembly 10 can be coiled during storage. FIG. 8A is a top view of an exemplary coiled configuration. In FIG. 8A, the urinary catheter 15 can be completely within the sheath 20. The rear end portion 65 of the sheath 20 can be proximate to the distal end portion 45 of the urinary catheter 15. The front end portion 60 of the sheath 20 can be proximate to the proximal end portion 35 of the urinary catheter 15. The catheter assembly 10 can be wrapped into a coil to provide for convenient storage. The front end portion 60 of the sheath 20 can be designed to include an introducer tip 70. The rear end portion 65 of the sheath 20 can be designed to include a sheath connector 80. In some embodiments, the catheter assembly 10 is configured such that the introducer tip 70 can be inserted into the sheath connector 80 during storage. In such embodiments, the sheath connector 80 can secure the introducer tip 70.

Figure 8B:
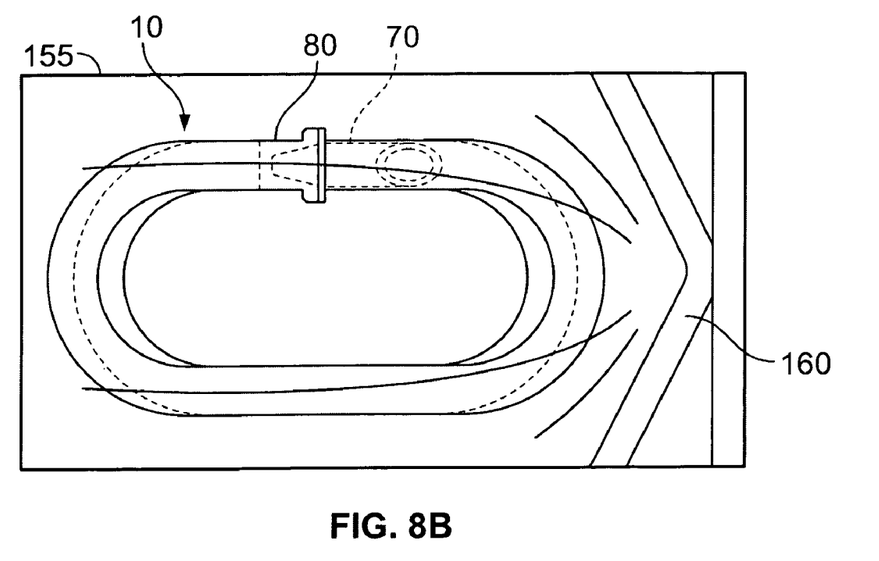
FIG. 8B is a top view of a packaged catheter assembly in a coiled configuration in which an introducer tip inserted into a sheath connector.

FIG. 8B shows a coiled configuration in which the introducer tip 70 is secured by the sheath connector 80. In FIG. 8B, the coiled catheter assembly 10 is enclosed within a package 155. The package 155 can be made of polyethylene, foil, Aclar®, metallized polyester, or other suitable material. The package 155 can be sealed by adhesive 160. The adhesive 160 can be made of ethyl vinyl acetate, hotmelt, acrylic adhesive, acrylic acid, acrylic acid formal, methyl, ethyl, n-propyl, butyl, pentyl, isopentyl, 2-methylbutyl, amyl, n-hexyl, 2-ethylbutyl, methylpentyl, heptyl, octyl, 2-ethylhexyl, n-decyl, isobornyl, n-undecyl, n-dodecyl, tridecyl, lauryl, stearyl, 10-cyclohexylundecyl, fusel oil, 6-methoxy, methoxyethyl, ethoxyethyl, methoxybutyl, methoxyethoxyethyl, polyoxyalkylene, hydroxymethyl, hydroxypropyl, butanediol, sodium polyethylene oxide, propylene glycol, glycol ether, tetrahydrofurfuryl, abitol, cyanoethyl, dimethylaminoethyl, glycidyl, benzophenoneglycidyl, 3-chloro-2-hydroxypropl, 3-(3,4-dichlorophenoxy)-2-hydroxypropyl, 3-(2,4,6-trichlorophenoxy)-2-hydroxypropyl, 3-(2,3,4,5-tetrachlorophenoxy)-2-hydroxypropyl, 3-(pentachlorophenoxy)-2-hydroxypropyl, sodium-2-sulfoethyl, dimethylaminoethyl, 1,6-hexanediol, glycol, diethyleneglycol, triethyleneglycol, tetraethyleneglycol, diethyleneglycol, trimethylolpropane, pentaerythritol, methacrylic acid, methacrylic acid formal, methyl, ethyl, butyl, pentyl, hexyl, octyl, 2-ethylexyl, n-nonyl, n-decyl, n-dodecyl, lauryl, isobornyl, hydroxythyl, hydroxypropl, methoxymethyl, methoxyethyl, ethoxyethyl, butoxyethyl, cyanoethyl, dimethylaminoethyl, t-butylaminoethyl, glycidyl, benzophenoneglycidyl, 3-(3,4-dicholorophenoxy)-2-hydroxypropyl, 3-)2,4,6-trichlorophenoxy)-2-hydroxypropyl, 3-(2,4,6-trichlorophenoxy)-2-hydroxypropyl, 3-(2,3,4,5-tetrachlorphenoxy)-2-hydroxypropyl, 3-(pentachlorophenoxy)-2-hydroxypropyl, 10-chlorodecyl, 2-sulfoethyl, sodium-2-sulfoethyl, 3-(trimethoxysilyl)propy, ethylene glycol, 1,3-butylene glycol, trietyhylene glycol, polyethylene glycol, dimethylaminoethyl, trimethylolethane, trimethylolpropane, pentaerythritol, acrylamide, N-methylol, N-ethanol, N,N-dimethyl, N-(1,1-dimethyl-3-oxobutyl), N-[2-(methyl-4-oxopentyl)], N-t-butyl, N,N-diacetonyl, octyl, N-t-C$_9$, N-t-C$_{12}$, N-[(2-ethylhexoxy)methyl], diacetone, diacetophenone, 2-isocyanate, 2-acrylamido-2-methylpropane sulfonic acid, methacrylamide, N-methylol, N,N-diacetonyl, N-(n-butoxymethyl), N-t-C$_{12}$, 2-isocyanate, trimethylamine, trimethylamine, triethylamine, tributylamine, 1,1-dimehtyl-1-(2-hdroxypropyl)amine, 1,1-dimethyl-1(2-hydroxypentyl)amine, 1,1-dimethyl-1-(2-hydroxyoctyl)amine, 1,1-dimethyl-1-(2-hydroxydecyl)amine, 1,1-dimethyl-1-(2,3-dihdroxypropyl)amine, 1-1-dimethyl-1-(2-hydroxy-3-phenoxypropyl)amine, 1,1-dimethyl-2-(2-hydroxy-3-isopropoxypropyl)amine, fumaric acid, monoisopryopl fumarate, diisopropyl fumarate, di-n-butyl fumarate, di-sec-butyl fumarate, diamyl fumarate, n-hexyl fumarate, di-2-ethylbutyl fumarate, diisoamylethylene fumarte, di-n-octyl fumarate, di-2-ethylhexyl fumarate, didodecyl fumarate, di-"Cellosolve" fumarate, bis(2-hydroxyethyl) fumarate, polypropylene glycol fumarate, fumaric acid amide, fumaric acid diamide, fumaric acid nitrile, fumaric acid dinitrile, crotonic acid, glycidyl crotonate, itaconic acid, itaconic anhydride, half esters of itaconic acid, citraconic acid, citraconicacid anhydride, half esters of citraconic acid, β-methacrylooxyloxyethyl acid succinate, maleic acid, maleic anhydride, methyl maleate, butyl maleate, dibutyl maleate, t-octyl maleate, di(2-ethylhexyl) maleate, bis(2-hydroxyethyl) maleate, maleic acid amide, maleic acid diaminde, N-methylol maleamide, maleic nitrile, maleic dinitrile, Primeene maleamic acid, N-methylol maleamic acid, N-t-C$_{12}$ maleamic acid, vinyl chloride, vinylidene chloride, vinyl acetate, vinyl propionate, vinyl butyrate, vinyl valerate, methyl vinyl ketone, vinyl toluene, vinyl benzoate, vinyl 10-phenylundeconoate, vinyl naphthalene, N-vinyl succinimide, N-vinylimidazole, 2-vinyl pyridine, 4-vinyl pyridine, N-vinyl pyrrolidone, N-vinyl piperidone, N-vinyl caprolactam, sodium vinyl sulfonate, vinyl methyl ether, vinyl ethyl ether, vinyl butyl ether, vinyl octyl ether, divinyl ether, 2-chlorethyl vinyl ether, tetraallyloxyethane, diallyl phthalate, diallyl succinate, tetraallyl ethane, tetraallyl silicate, allyl glycidyl ether, triallylcyanurate, triallylisocyanurate, styrene, α-methylstyrene, t-butylstyrene, methacrylate terminated polystyrene macromolecular monomer, β-propiolactone, δ-valerolactone, ε-caprolactine, diketene, alkenyl azlactone, 3-[(2-acryloxyethyl)dimethyl ammonium]propionate betaine, 3-[(2-acryloxyethyl)dimethyl ammonium]propanesulfonate betaine, 3-[(2-methacryloxyethyl)dimethyl ammonium]propionate betaine, methylenebisphenyl-4-4'-diisocyanate, acrylic acid-2-isocyanate ester, polyisocyannate perpolymers, 3-mthacryloxypropyltrimethoxysilane, or other suitable material.

In some embodiments, the package 155 can be designed to be hermetically sealed. In such embodiments, the hermetically-sealed package 155 can prevent pre-lubricated catheter assemblies from drying out during storage. In some embodiments, the package 155 can be designed such that it fits within a user's pocket for convenient transport. In such embodiments, the user's pocket can be roughly seventeen centimeters in length, twelve centimeters in width, and three centimeters in thickness. One or more packages 155 can be stored within a container. The container can be made of foil, a combination of polyurethane and foil, metallized polyester, Aclar®, or other suitable material. The container can be designed to be hermetically sealed. The hermetically-sealed container can prevent packages containing pre-lubricated catheter assemblies from drying out during storage.

Referring again to FIG. 1, other storage configurations are also possible. For example, the catheter assembly 10 can be stored in an un-coiled, straight configuration. The catheter assembly 10 can be folded for storage. The catheter assembly can be coiled tighter or looser than shown in FIGS. 8A-8B. The catheter assembly 10 can be stored within a package. The package can be designed to be relatively rigid. The package can be flexible. Multiple catheter assemblies 10 can be stored within a package. The package can be a collection cup. In some embodiments, the collection cup can be made of expandable material. In such embodiments, the collection cup can be stored in a generally flat configuration with the catheter assembly 10 inside. In such embodiments, a user can remove the catheter assembly 10 from the collection cup. In such embodiments, the user can expand the collection cup, preparing it to collect urine. In such embodiments, the user can attach the catheter assembly to the collection cup during use.

Figure 9A:
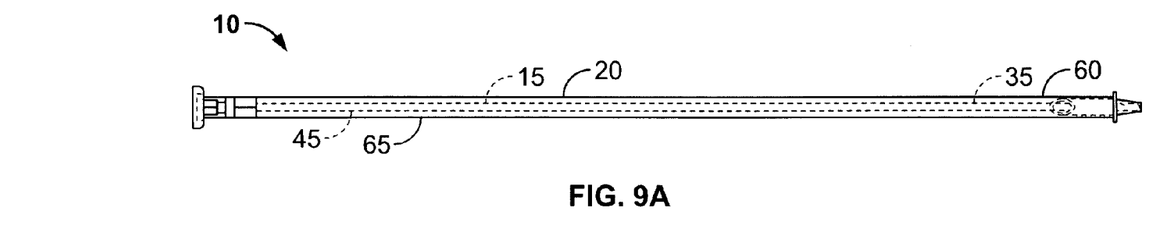
FIG. 9A is a side view of a catheter assembly in an uncoiled storage position.
Figure 9B:
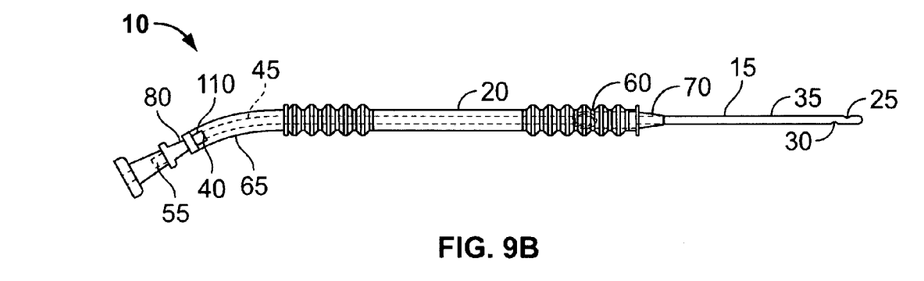
FIG. 9B is a side view of a catheter assembly in a use position.
Figure 9C:
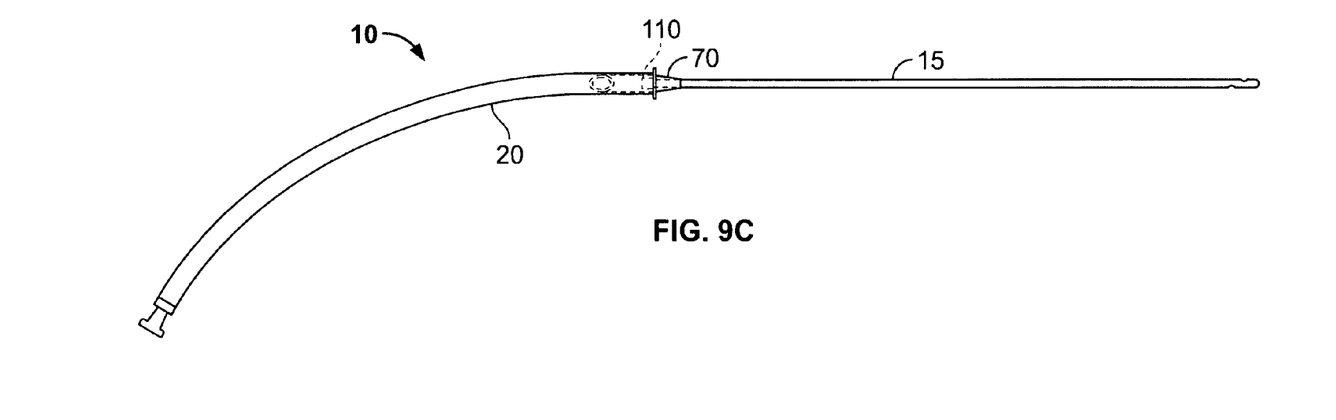
FIG. 9C is a side view of a catheter assembly in a fully-extended use position.

FIGS. 9A-9C are side views of the catheter assembly 10 of FIG. 1 in three different positions. FIG. 9A shows the catheter assembly 10 in an un-coiled storage position. As shown, the urinary catheter 15 is completely within the sheath 20. Also as shown, the proximal end portion 35 of the urinary catheter 15 is proximate to the front end portion 60 of the sheath 20, and the distal end portion 45 of the urinary catheter 15 is proximate to the rear end portion 65 of the sheath 20.

FIG. 9B shows the catheter assembly 10 in use. As shown, a user—a patient or a caregiver—has pushed the proximal end portion 35 of the urinary catheter 15 through the opening 50 in the front end portion 60 of the sheath 20. The user has also pushed the proximal end portion 35 of the urinary catheter through the introducer tip 70. The catheter assembly 10 can be designed such that a user need not touch the urinary catheter 15 directly with his or her hands. Hands-free use can be more sanitary and can, thereby, reduce the number of urinary tract infections. A user can accomplish this in several ways. For example, a user can grip the sheath 20 and the underlying section of the urinary catheter 15 roughly fifteen centimeters from the introducer tip 70 with his or her left hand. At the same time, the user can grip the sheath 20 and the underlying section of the urinary catheter 15 roughly five centimeters from the introducer tip 70. The user can grip the sheath 20 and the urinary catheter 15 firmly with his or her left hand to prevent them from moving relative to each other. The user can grip the sheath 20 and the urinary catheter 15 less firmly with his or her right hand to allow the urinary catheter 15 to move relative to the sheath 20. The dimensions provided are exemplary. The user can grip at any two positions that permit the user to slide the urinary catheter 15 within the sheath 20. The user can then move his or her left hand toward his or her right hand, such that the sheath 20 remains in a fixed position within his or her right hand while the urinary catheter 15 slides through his or her right hand out of the introducer tip 70.

In some cases, the user will have aligned the introducer tip 70 with a urethral meatus—either his or her own, or that of a patient to whom the user is giving care. When the urinary catheter 15 slides out of the introducer tip 70, the urinary catheter 15 can slide through the urethral meatus and into the urethra. The user can insert more of the urinary catheter 15 into the urethra. To continue with the example posited above, the user can grip firmly with his or her right hand to prevent relative motion between the sheath 20 and the underlying section of the urinary catheter 15. Then the user can release his or her left-hand grip. The user can then grip the sheath 20 with his or her left hand and pull the sheath 20 toward the distal end portion 45 of the urinary catheter 15 while the urinary catheter 15 remains substantially stationary. The user can then release his or her left-hand grip of the sheath 20. The user can re-grip the sheath 20 and the underlying section of the urinary catheter roughly ten centimeters closer to the sheath connector 80 than the right-hand grip. The user can then repeat the process described above. Again, the dimensions provided are exemplary. The user can grip at any two positions that permit the user to slide the urinary catheter 15 within the sheath 20.

As the user continues to push more of the urinary catheter 15 through the introducer tip 70, the urinary catheter 15 encounters the bladder. When the openings 25, 30 in the proximal end portion 35 of the urinary catheter 15 enter the bladder, urine can start to drain. Urine can drain into the openings 25, 30 in the proximal end portion 35 of the urinary catheter 15 out of the opening 40 in the distal end portion 45 of the urinary catheter 15, and out of the opening 55 in the rear end portion 65 of the sheath 20. As the urine drains, the urine can pass through the catheter connector 110 and then through the sheath connector 80.

In some embodiments, the distal end portion 45 of the urinary catheter 15 is fixedly connected to the rear end portion 65 of the sheath 20. In such embodiments, the user can continue to move the front end portion 60 of the sheath 20 toward the back end portion 65 of the sheath 20. The sheath 20 can be designed to collapse on itself, resulting in the entire sheath 20 being bunched proximate to the distal end portion 45 of the urinary catheter during the draining process.

As shown, the catheter connector 110 is still connected to the sheath connector 80. The user can disconnect the catheter connector 10 from the sheath connector 80. To continue with the example posited above, the user can grip the front end portion 60 of the sheath 20 and the underlying section of the urinary catheter 15 firmly with his or her right hand. At the same time, the user can grip the rear end portion 65 of the sheath 20 and the distal end portion 45 of the urinary catheter 15 less firmly with his or her left hand. Then, the user can move his or her left hand away from his or her right hand, maintaining the front end portion 60 of the sheath 20 and the underlying section of the urinary catheter 15 in a substantially fixed position. This movement can allow the catheter connector 1 0 to disengage from the sheath connector 80 as the rear end portion 65 of the sheath 20 slides off the distal end portion 45 of the urinary catheter 15.

As soon as the user inserts enough of the urinary catheter 15 into the urethra such that the openings 25, 30 in the proximal end portion 35 enter the bladder, the user can begin the draining process. The user can wait to insert the urinary catheter 15 that far into the urethra until he or she is ready for urine to begin draining. As such, a user can first, for example, fasten the sheath connector 80 to a drainage receptacle. The user can first connect the sheath connector 80 to an extension tube or a collection bag. The user can first move the sheath 20 away from the patient to make sure the rear end portion 65 of the sheath 20 can reach the drainage receptacle. In some cases, the user can first fully extend the sheath such that the distance from the end of the proximal end portion 35 of the urinary catheter 15 to the end of the rear end portion 65 of the sheath 20 is nearly equal to the length of the urinary catheter 15 plus the length of the sheath 20. FIG. 9C illustrates such a case. In such cases, the user can connect to the catheter connector 110 to the introducer tip 70. In such cases, the interface between the catheter connector 110 and the introducer tip 70 can form a liquid-tight seal. When the user completes his or her various preliminary steps, he or she can begin the drainage process.

To remove the urinary catheter 15 from the bladder and out of the urethra, the user can reverse the process described above. The user can alternate gripping more or less with one hand than with the other hand, and moving one hand toward or away from the other hand. In some embodiments, the user can retract the urinary catheter 15 until it is completely within the sheath 20. In some embodiments, removing the urinary catheter 15 according to this process can reduce or eliminate the user's need to touch the urinary catheter with his or her hand. In such embodiments, the cathing process can be substantially more sanitary.

In some embodiments, the urinary catheter 15 can be removed from the bladder while fully extended out of the sheath 20. A user can grip the distal end portion 45 of the urinary catheter 15 and pull the urinary catheter 15 from the bladder. In such embodiments, the user can insert the proximal end portion 35 into the opening 55 of the rear end portion 65 of the sheath 20. The user can insert the entire urinary catheter 15 into the sheath 20 through the opening 55 of the rear end portion 65 such that the front end portion 60 of the sheath 20 meets the rear end portion 65 of the sheath 20, thereby forming a loop. The catheter assembly can be secured in such a loop configuration for disposal.

The urinary catheter 15 can be lubricated before being inserted into the urethra. The lubrication can be any water-based lubricant, such as Lubrajel®, KY® Gel, silicon fluid, or other suitable substances. A user can move a section of the urinary catheter 15 out of the sheath 20 and apply lubrication to the urinary catheter 15. The user can wipe, squirt, or spray lubrication on the urinary catheter 15.

In some embodiments, the urinary catheter 15 is designed to be pre-lubricated. Pre-lubrication can allow users to move the urinary catheter 15 directly from the sheath 20 into the urethra with no intermediate lubrication phase. Pre-lubrication can eliminate the need for users to handle lubrication with their hands—a process that can be messy. Pre-lubrication can eliminate the need for users to carry lubrication with them. Prior to pre-lubricating the urinary catheter 15, the urinary catheter can be stripped of residue and other contaminants. Such stripping can involve steam cleaning, chemically cleaning, or other suitable methods, or combinations thereof. Urinary catheters can be pre-lubricated in various ways. For example, the urinary catheter 15 can be placed within the sheath 20, and the sheath 20 can be injected with lubrication. The urinary catheter 15 can be dipped in lubrication before being placed within the sheath 20. Lubrication can be wiped onto the surface of the urinary catheter 15 before insertion into the sheath 20. Lubrication can be sprayed onto the surface of the urinary catheter 15 before insertion into the sheath 20. Other suitable ways of pre-lubricating urinary catheters can be implemented. Various amounts of lubricant can be applied to the urinary catheter 15 as part of the pre-lubrication process. For example, in catheter assemblies in which the sheath 20 is approximately fifty-five centimeters and the urinary catheter 15 is approximately 46 centimeters, 2 grams, 1.5 grams, 1 gram, or any other suitable amount of lubricant can be applied to the urinary catheter 15. For example, a catheter can contain between 1.5 grams and 0.5 grams of water-based lubricant.

In some embodiments, the urinary catheter 15 can be corona treated before being lubricated. Corona treatment can involve exciting the outer surface of the urinary catheter 15 to increase the surface tension of the outer surface of the urinary catheter 15. This can make the urinary catheter 15 more receptive to lubrication. With the outer surface of the urinary catheter 15 in an excited condition, lubrication can be applied. Lubrication can be applied in any of the ways described above or in any other suitable way. After a period of time, the outer surface of the urinary catheter 15 resumes its normal shape. This can result in a more uniform coating of lubrication across the surface of the urinary catheter 15.

Although a number of embodiments have been described, it will be understood that various modifications are possible. Accordingly, other embodiments are within the scope of the following claims.

What is claimed is:

1. An apparatus comprising:
    a urinary catheter having a proximal end portion defining a urine inlet opening and a distal end defining a urine outlet opening;
    a sheath having a front end portion defining a front opening and a rear end defining a rear opening, and a rear end connector attached to said rear end of said sheath to define a discharge end of the apparatus; and
    a suction cup attached directly to said rear end connector wherein, during use, said suction cup secures said discharge end of the apparatus to a surface of a toilet;
    wherein said apparatus is configured such that at least a portion of said urinary catheter is within said sheath during storage and use,
    wherein said apparatus is configured such that said distal end of said urinary catheter moves toward said front end portion of said sheath during use, thereby increasing the distance between said distal end of said urinary catheter and said rear end of said sheath, and
    wherein, during use, urine flows into said urine inlet opening, out of said urine outlet opening, and out of said rear opening.

2. The apparatus of claim 1, wherein said urinary catheter is between fifteen and fifty-five centimeters in length.

3. The apparatus of claim 1, wherein said urinary catheter is made of polyvinyl chloride.

4. The apparatus of claim 1, wherein said proximal end portion defines a second urine inlet opening.

5. The apparatus of claim 1, wherein said urine outlet opening is oval-shaped.

6. The apparatus of claim 1, wherein said distal end defines said urine outlet'opening at the end of said urinary catheter.

7. The apparatus of claim 1, wherein said sheath is made of polyvinyl chloride.

8. The apparatus of claim 1, wherein said front end portion defines said front opening at the end of said sheath.

9. The apparatus of claim 1, wherein said apparatus is configured such that said urinary catheter is completely within said sheath during storage.

10. The apparatus of claim 9, wherein said front opening and said rear opening are sealed during storage.

11. The apparatus of claim 1, wherein said apparatus is configured such that, during storage, said proximal end portion is proximate to said front end portion and said distal end is proximate to said rear end.

12. The apparatus of claim 1, wherein said apparatus is configured such that at least a portion of said urinary catheter remains within said sheath during use.

13. The apparatus of claim 1, wherein, during use, urine flows out of said urine outlet opening, along a lumen of said sheath toward said rear opening, and out of said rear opening.

14. The apparatus of claim 1, further comprising a package enclosing said urinary catheter and said sheath.

15. The apparatus of claim 14, wherein said urinary catheter and said sheath are coiled inside said package.

16. The apparatus of claim 14, wherein said package comprises a sealed package.

17. The apparatus of claim 1, further comprising a distal end connector defining a distal connector opening, said distal end connector being attached to said distal end.

18. The apparatus of claim 17, further comprising a front end connector defining a front connector opening, said front end connector being attached to said front end portion.

19. The apparatus of claim 18, wherein, during use, said apparatus is configured such that said distal end connector interfaces with said front end connector, thereby forming a seal to allow urine to flow out of said urine outlet opening, through said distal connector opening and said front connector opening, and out of said rear opening.

20. The apparatus of claim 1, further comprising:
    an extension tube attachable to said rear end connector.

21. The apparatus of claim 1, further comprising a handle attached to said rear end connector that is operable to disengage said rear end connector from said toilet.

22. The apparatus of claim 1, further comprising an introducer tip defining an insertion opening, said introducer tip being attached to said front end portion of said sheath, said apparatus configured such that said proximal end portion of said urinary catheter protrudes through said front opening of said sheath to communicate with said insertion opening.

23. The apparatus of claim 1, further comprising lubrication, wherein said urinary catheter is coated by said lubrication.

24. The apparatus of claim 23, wherein said lubrication comprises a water-based lubricant.

* * * * *